(12) United States Patent
Boehm (10) Patent No.: US 11,064,961 B2
(45) Date of Patent: Jul. 20, 2021

(54) SYSTEMS AND METHOD FOR A MOBILE IMAGING UNIT

(71) Applicant: General Electric Company, Schenectady, NY (US)

(72) Inventor: Manfred David Boehm, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 366 days.

(21) Appl. No.: 16/045,544

(22) Filed: Jul. 25, 2018

(65) Prior Publication Data
US 2020/0029922 A1  Jan. 30, 2020

(51) Int. Cl.
*A61B 6/00* (2006.01)

(52) U.S. Cl.
CPC .......... *A61B 6/4476* (2013.01); *A61B 6/4405* (2013.01); *A61B 6/547* (2013.01)

(58) Field of Classification Search
CPC .................................................. A61B 6/4405
See application file for complete search history.

(56) References Cited

U.S. PATENT DOCUMENTS

| 6,409,382 | B1 | 6/2002 | Akutsu et al. |
| 7,682,077 | B2 | 3/2010 | Halsmer et al. |
| 2011/0249805 | A1 | 10/2011 | Kralles |
| 2014/0093051 | A1* | 4/2014 | Nishimura ........... A61B 6/4405 378/198 |

FOREIGN PATENT DOCUMENTS

| JP | 2011125580 A | 6/2011 |
| JP | 2015112387 A | 6/2015 |

OTHER PUBLICATIONS

EP application 19187677.0 filed Jul. 22, 2019—Search Report dated Apr. 17, 2020, 14 pages.
JP 2011125580—English translation of Abstract; Espacenet search Jun. 26, 2020; 1 page.

* cited by examiner

*Primary Examiner* — Dani Fox
(74) *Attorney, Agent, or Firm* — McCoy Russell LLP (57) ABSTRACT

Methods and systems are provided for controlling movement of a mobile imaging system. In one example, a mobile imaging system includes a mobile drive system, an imaging assembly coupled to the mobile drive system, and a driving interface configured to move the imaging assembly relative to the mobile drive system both axially and radially in response to user manipulation, and further configured to generate signals in response to the axial movement of the imaging assembly, the mobile drive system configured to move in response to the signals.

20 Claims, 5 Drawing Sheets

SYSTEMS AND METHOD FOR A MOBILE IMAGING UNIT

FIELD

Embodiments of the subject matter disclosed herein relate to mobile imaging systems, and more particularly to positioning a mobile imaging system prior to scanning a patient.

BACKGROUND

Mobile imaging systems, such as mobile x-ray devices, are often mounted on motorized carts that are driven to the patient's location. The cart typically has two main wheels in the rear that are driven to move the system. Two swivel wheels are usually provided in the front of the cart. Additionally, the imaging assembly (such as the x-ray source or tube) is mounted on a swivel column proximate the front of the unit.

In these mobile imaging systems, the movable unit or cart has independently driven wheels that allow for some degree of steering. A drive handle may be provided at the rear of the cart, allowing the operator to push harder on one side or the other of the handle, resulting in the cart turning one direction or the other.

Using the rear drive handle, the operator can drive to a location, position the cart proximate to the patient's bed, and position the imaging assembly to image an anatomy of interest. When positioning the imaging assembly, the operator is often at the assembly-side of the system (e.g., the tube-side in a mobile x-ray device), which may be on the other side of the patient's bed from the movable unit. Therefore, if the movable unit is not in the correct position, the operator has to return to the back side of the movable unit and attempt to position the unit such that the imaging assembly is properly aligned with the anatomy. This adjustment process can be very time consuming. In addition, some patient rooms are quite small and/or the available area in which to move the system is limited, such as by other patient monitoring devices and machines.

BRIEF DESCRIPTION

In one embodiment, a mobile imaging system includes a mobile drive system, an imaging assembly coupled to the mobile drive system, and a driving interface configured to move the imaging assembly relative to the mobile drive system both axially and radially in response to user manipulation, and further configured to generate signals in response to the axial movement of the imaging assembly, the mobile drive system configured to move in response to the signals.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The present disclosure relates to a mobile imaging system that implements an intuitive positioning aid while an operator is setting up for a medical imaging session. In an example, an imaging assembly (such as an x-ray source) is attached to a rotatable column via a horizontal arm. The arm may have a finite range of motion both toward and away from the column. When the end of travel of the arm is reached, either toward or away from the column, drive wheels of a drive system of the mobile imaging system are activated to move the mobile imaging system away from or toward the operator. When the imaging assembly has reached the desired position, the operator may cease any push or pull movement and the system may deactivate the drive wheels to stop motion of the mobile drive system. In this way, the mobile drive system may be moved according to an intuitive work flow where intrusive user input to an input device to command movement is dispensed with or reduced, and thereby the operator does not have to consciously think about which user input to apply to which input device to achieve the desired movement of the mobile imaging system.

Figure 1:
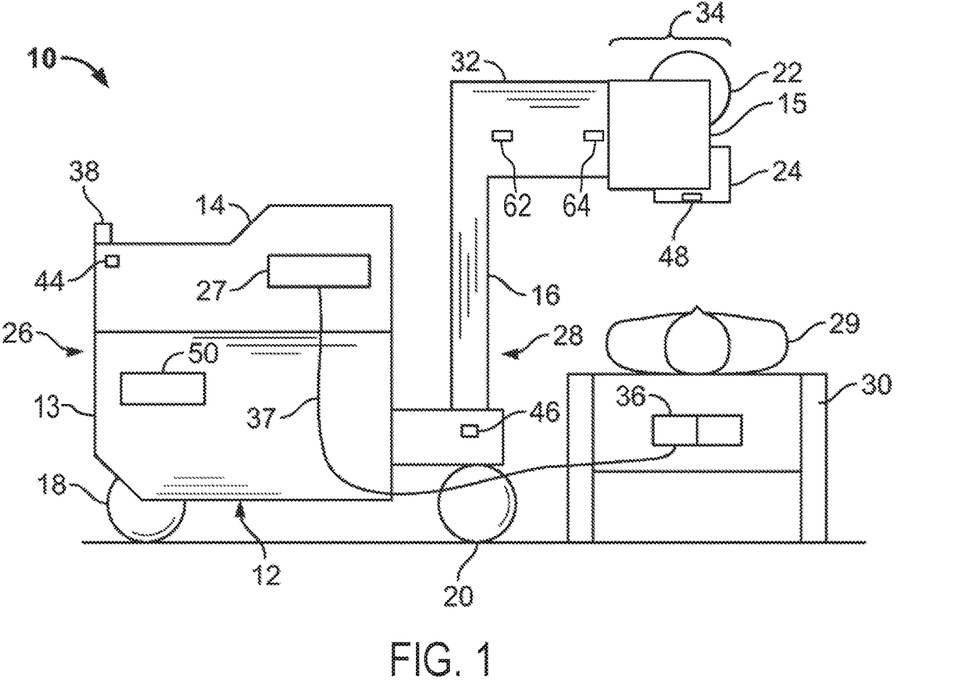
FIG. 1 is an elevation view of an example mobile imaging system.

FIG. 1 illustrates a mobile imaging system 10 that may be used in the medical field or in other fields. The system 10 has a wheeled motorized drive assembly 12 and an operator console 14 that may be supported by the drive assembly 12. The motorized drive assembly 12 comprises a frame 13 (also referred to herein as a cart) and two rear drive wheels 18 (one wheel is shown) coupled to the frame at a rear end 26 of the system 10 and two front wheels 20 (one wheel is shown) coupled to the frame at a front end 28 of the system 10.

A column 16 or other support member is attached to, and extends upwardly from, the frame of drive assembly 12 and rotates or swivels with respect to the drive assembly 12. In some examples, column 16 is collapsible and thus may be comprised of multiple, nested sections that may telescope outward from the frame in response to user manipulation. A sensor 46 may detect the amount of rotation or movement of the column 16 with respect to the drive assembly 12. An arm 32 is fixed to the column 16 at a predetermined rotational position. The arm 32 may be vertically adjustable relative to the frame. For example, the column may be collapsible (as described above) and the arm 32 may be moved vertically as the column is extended or collapsed. Additionally or alternatively, the arm may be configured to translate vertically along the column 16, e.g., in response to user manipulation. The arm 32 may also telescope with respect to the column 16, allowing components mounted at an outer end of the arm 32 to be moved closer to or further away from the column 16. In one embodiment, the arm 32 may have further degrees of freedom with respect to the column 16. An imaging assembly, herein in the form of a radiation source 34 including an x-ray source assembly 15, is attached to the outer end of the arm 32 and has an x-ray tube housing 22 containing an x-ray source (not shown). A collimator 24 is attached to the tube housing 22 and is rotatable with respect to the tube housing 22. A sensor 48 may be provided to detect the amount of rotation or movement of the collimator 24 with respect to the drive assembly 12 and/or column 16. An x-ray detector 36 detects x-ray data and may communicate with an imaging controller 27 wirelessly or over a cable 37.

One or more sensors are positioned to detect relative movement of the arm 32, e.g., relative to the column 16. As shown, a push sensor 62 may detect movement of the arm 32 inward toward the column 16 and a pull sensor 64 may detect movement of the arm 32 outward away from the column 16. The push sensor 62 may be positioned proximate the column 16 (e.g., closer to the column than the imaging assembly) while the pull sensor 64 may be positioned proximate the imaging assembly (e.g., closer to the radiation source 34 than the column 16). However, the placement of the sensors is exemplary, and other positions are possible, such as the push sensor being positioned proximate the imaging assembly while the pull sensor is positioned proximate the column.

Push sensor 62 and pull sensor 64 may each be a mechanical switch that indicates an end of travel of the arm. In other examples, push sensor 62 and pull sensor 64 may be optical sensors, magnetic sensors, pressure/force sensors, inertial measurement units (IMUs), or any variation of these sensors. If the sensors are potentiometers or encoders, the degree of extension of the arm may be measured continuously, with end of travel positions defined by predefined values within the extension range. It should be noted that the sensors of the various embodiments may be a suitable type or types of sensors. For example, one or more of the sensors may operate based on sensing a change in distance using optical, magnetic, electrical, or other mechanisms.

A first hand-actuatable interface is provided on system 10, herein in the form of a drive handle 38 provided on the rear end 26 of the system 10, such as coupled to the frame of drive assembly 12. A drive controller 50 senses or receives signals based on the manipulation (e.g., user manipulation) of the drive handle 38, and thus the system 10 may be driven to different locations to image a subject 29. The drive assembly 12 may have at least one motor (shown in FIG. 2) and is capable of driving the rear drive wheels 18 separately.

The subject 29 is typically lying on a bed or table 30. Once the system 10 is positioned near the table 30, the column 16 is swiveled or rotated (e.g., via user manipulation) to position the x-ray source assembly 15 over the subject 29. The detector 36 is positioned on the opposite side of the subject 29.

A user interface 44 may be provided proximate the rear end 26 of the system 10. Optionally, the user interface 44 may be integrated with the drive handle 38 or it may be configured as a remote control that may be held in the operator's hand away from the system 10. The user interface 44 may communicate with the drive controller 50 wirelessly or over a wired connection. The user interface 44 may be one of, or a combination of, a button, joystick, toggle switch, power assist handle, provided as a key on a keyboard or a selection on a touchscreen, and the like. In some examples, the user interface 44 may be in the form of the drive handle 38. In such an example, manipulation of the drive handle 38 may result in signals being sent to the drive controller 50 to control movement of the system 10. In some examples, the signals sent by the drive handle 38 may be different than the signals sent by the user interface 44. For example, the user interface 44 may send signals to switch drive modes, power on or off the system 10, etc.

The drive controller 50 receives angle information from the sensor 46 and the sensor 48 that indicates the position of the column 16, arm 32, collimator 24, and/or x-ray source assembly 15. Further, drive controller 50 receives arm movement information from sensors 62 and 64 that indicates the extension/movement of the arm (and the associated movement of the imaging assembly coupled to the arm). When the operator moves the imaging assembly and/or arm to an end-of-travel position (e.g., where telescoping motion of the arm stops and further movement of the arm is transmitted to the column), the system 10 may be moved based on, for example, the angle of rotation of the column 16 with respect to the drive assembly 12 and the direction of movement of the arm. In another embodiment, the collimator 24 may be rotated or adjusted with respect to the x-ray tube housing 22. Therefore, the angle relationship between the collimator 24 and the drive assembly 12 will also change. The drive controller 50 may then move the system 10 (e.g., engage motor(s) within the drive assembly 12 to cause the rear drive wheels 18 to move and/or rotate the column 16) based on the angle of rotation of the collimator 24 with respect to the drive assembly 12. It should be understood that different angles of rotation with respect to the drive assembly 12 may be used.

Figure 2:
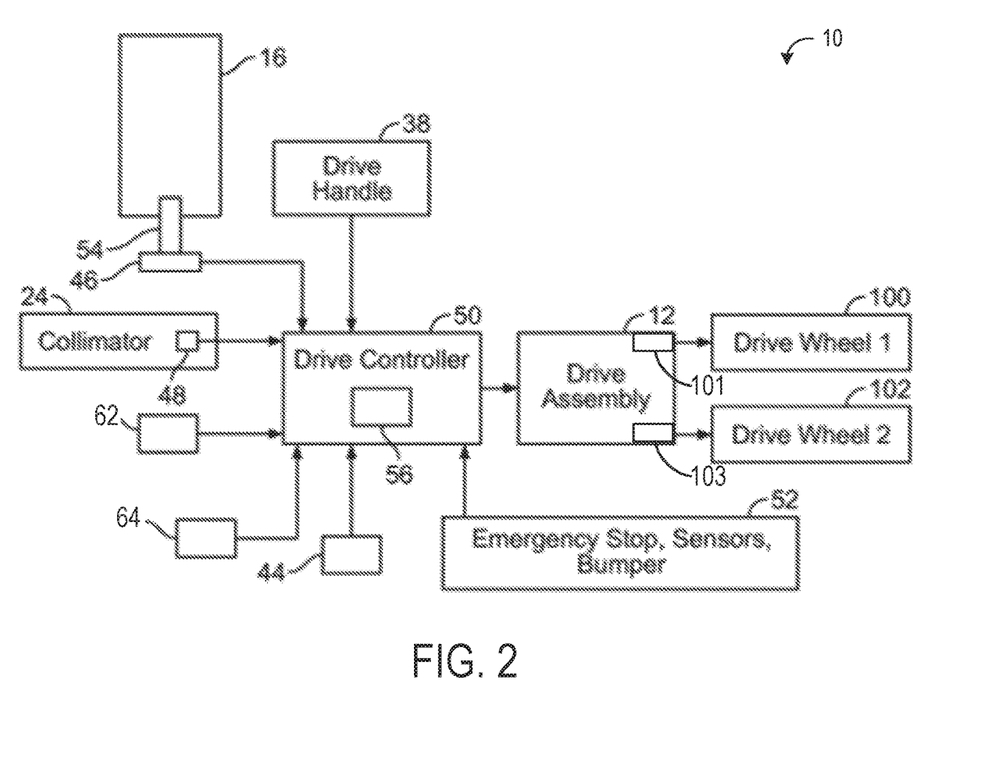
FIG. 2 is a block diagram of the components for rotation-based driving of the system of FIG. 1.

FIG. 2 is a block diagram of the components for rotation-based driving of the system 10 of FIG. 1. As discussed previously, when moving to another room and during initial positioning, the drive controller 50 receives drive input(s) from the drive handle 38. Based on the drive input(s), the drive controller 50 outputs velocity information to the drive assembly 12 to drive each of first and second drive wheels 100 and 102 (which in one embodiment are the rear drive wheels 18 shown in FIG. 1) via first motor 101 and second motor 103, respectively. At any time during operation, the drive controller 50 may be configured to receive and act upon an input from one or more emergency stop mechanisms 52, which may include one or more of a button, sensor, bumper and the like.

In one embodiment, the bottom of the column 16 is connected to a shaft 54 that extends from the drive assembly 12. The sensor 46 is connected to the shaft 54 to detect the rotation of the column 16. The sensor 46 provides the rotation information to the drive controller 50. The sensor 46 may be an optical sensor, magnetic sensor, Hall effect sensor, or other suitable sensor adapted to detect the degree of rotation of column 16. It should be understood that other encoder or sensor configurations may be used to sense the rotation of the column 16. The sensor 48 mounted to or proximate the collimator 24 senses rotation of the collimator 24 and provides the rotation information to the drive controller 50. Sensor 62 and sensor 64 are located on or within arm 32 and sense movement of the arm (and associated imaging assembly), and provide arm extension/movement information to the drive controller 50. In one example, sensor 62 may provide output to the drive controller 50 that the drive controller 50 may use to determine if the arm has reached a first end-of-travel position. Sensor 64 may provide output to the drive controller 50 that the drive controller 50 may use to determine if the arm has reached a second end-of-travel position. The sensor 46, the sensor 48, the sensor 62, and the sensor 64 may communicate with the drive controller 50 wirelessly or over wired connections.

When the drive controller 50 receives input from sensor 62 and/or sensor 64, a rotation-based drive module 56 of drive controller 50 may determine the velocities for each of the first and second drive wheels 100 and 102 based on the rotation information provided by one or both of the sensors 46 and 48, as well as the particular input from the sensors 62 and 64 indicating a direction of movement of the arm/radiation source (e.g., toward or away from the operator), as described in more detail below.

Figure 3:
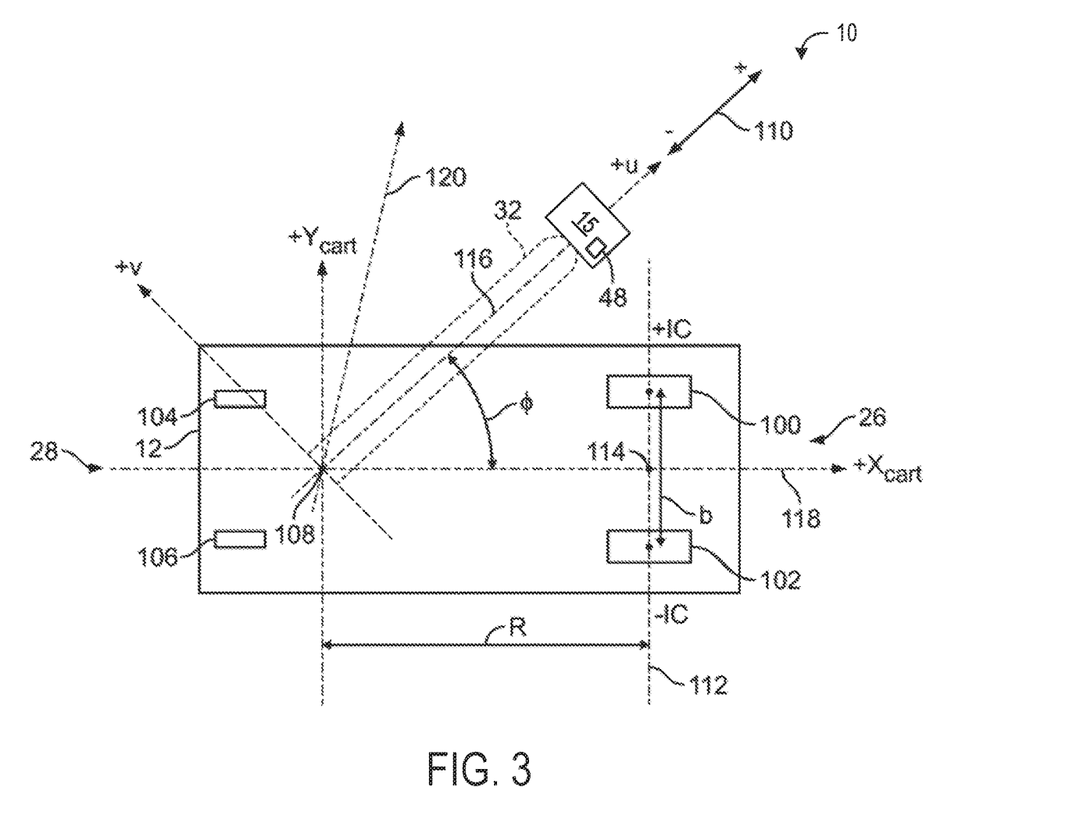
FIG. 3 is a schematic diagram illustrating the orientation of the drive assembly and column of the mobile imaging system of FIG. 1.

FIG. 3 is a schematic diagram illustrating the orientation of the drive assembly 12 and column 16 with respect to each other. First and second drive wheels 100 and 102 are shown proximate the rear end 26 of the drive assembly 12. First and second swivel wheels 104 and 106 are shown proximate the front end 28 of the drive assembly 12. A distance b between the first and second drive wheels 100 and 102 is indicated.

The drive assembly 12 may have a coordinate system Xcart, Ycart. Longitudinal axis 118, corresponding to Xcart, extends parallel to the length of the drive assembly 12 and is centered between the first and second drive wheels 100 and 102. The column 16 (not shown in FIG. 3) pivots with respect to the drive assembly 12 at pivot point 108. For example, referring to FIG. 2, a center of the column 16 or the shaft 54 may define the pivot point 108. The column 16 may have a coordinate system u, v. The pivot point 108 is the point of origin for both of the coordinate systems. As shown in FIG. 3, the column 16 is pivoted with respect to the longitudinal axis 118 such that a center line 116 of the arm 32 (corresponding to the u axis) is at an angle of rotation Φ with respect to the longitudinal axis 118. As used herein, the angle of rotation Φ is equal to zero when the +u axis is coincident with the Xcart axis (e.g., when the longitudinal axis of the arm is aligned with the longitudinal axis of the frame of the mobile imaging system). The angle of rotation Φ may increase (with positive values) as the column is rotated clockwise and increase with negative values as the column is rotated counter clockwise.

The first and second drive wheels 100 and 102 are positioned along drive axis line 112. A distance R is indicated between a center point 114 along the drive axis line 112 between the first and second drive wheels 100 and 102 and the pivot point 108.

By way of example, the operator may position the x-ray source assembly 15 over the subject 29 (e.g., by manipulating the drive handle 38) and may desire to move the x-ray source assembly 15 along the u axis, which is also referred to herein as the radiation source axis. The positive and negative movement directions along the u axis are indicated with arrow 110. If the arm is telescopic or otherwise movable, the operator may move the x-ray source assembly 15 manually, between the first end-of-travel position and the second end-of-travel position. However, once an end-of-travel position is reached, manual movement of the x-ray source assembly 15 ceases and further movement along the u axis may be accomplished by automatically driving, with the drive assembly 12, the first and second drive wheels 100 and 102 with respective velocities based on the angle Φ. The velocity includes a speed component, which may be measured, for example, in millimeters (mm) per second, and a direction component (e.g., forward and backward). Forward may be defined as towards the front end 28 of the drive assembly 12 and backward may be defined as towards the rear end 26 of the drive assembly 12.

If the first and second wheels 100 and 102 are driven with different velocities, the drive assembly 12 will rotate about an instant center (IC), which is located at some point along the drive axis line 112. For example, if the speed at each of the first and second drive wheels 100 and 102 is equal but in opposite directions, then the IC equals 0, which is the center point 114 between the two wheels 100 and 102. Positive values of IC are located along the drive axis line 112 to the side of the first drive wheel 100 and negative values of IC are located along the drive axis line 112 to the side of the second drive wheel 102. If the velocity at the first drive wheel 100 is zero and the velocity at the second drive wheel 102 is not zero, then IC equals b/2, which is located at the first drive wheel 100. If the velocity at the first drive wheel 100 is not zero and the velocity at the second drive wheel 102 is zero, then IC equals −b/2 and is located at the second drive wheel 102.

The output from sensors 62 and 64 may be used to determine a desired direction of movement of the x-ray source assembly 15. For example, sensor 62 may detect that the arm has been moved to a first end-of-travel position where the arm is at a shortest possible length, indicating that the operator desires to move the x-ray source assembly toward the pivot point 108. Sensor 64 may detect that the arm has been moved to a second end-of-travel position where the arm is at a longest possible length, indicating that the operator desires to move the x-ray source assembly away from the pivot point 108.

When the output from sensors 62 and 64 indicate the operator desires to move the x-ray source assembly 15 away from the pivot point 108 (e.g., toward the operator), the rotation-based drive module 56 may determine the velocities of the first and second drive wheels based on the following equations:

$$V_1 = b*V_t*\sin\Phi 2R - V_t*\cos\Phi \qquad \text{Eq. 1}$$

$$V_2 = -b*V_t*\sin\Phi/2R - V_t*\cos\Phi \qquad \text{Eq. 2}$$

Wherein $V_1$ and $V_2$ are velocities of the first and second drive wheels 100 and 102, respectively. When $V_1$ or $V_2$ is positive, the associated drive wheel is driven forward and when $V_1$ or $V_2$ is negative, the associated drive wheel is driven backward. The distance between the first and second drive wheels 100 and 102 is b, R is the distance between the drive axis line 112 and the pivot point 108 of the column 16, and $V_t$ is the desired magnitude of velocity at the pivot point 108.

When the output from sensors 62 and 64 indicate the operator desires to move the x-ray source assembly 15 toward the pivot point 108 (e.g., away from the operator), the rotation-based drive module 56 may determine the velocities of the first and second drive wheels based on the following equations:

$$V_1 = -(b*V_t*\sin\Phi/2R - V_t*\cos\Phi) \qquad \text{Eq. 3}$$

$$V_2 = -(-b*V_t*\sin\Phi/2R - V_t*\cos\Phi) \qquad \text{Eq. 4}$$

As shown in FIG. 3, Φ is the angle of rotation of the column 16 with respect to the longitudinal axis 118. However, Φ may be selected to be along the v axis, such as by selecting an input on the user interface 44, and the drive controller 50 effectively calculates the angle by adding 90 degrees to the angle of the column 16 (Φ as shown in FIG. 3). Other driving directions may be achieved, such as by determining Φ based on the angle of rotation of the column 16 as well as the angle of rotation of the collimator 24. For example, the collimator sensor 48 may detect motion of the collimator with respect to the u axis. In another embodiment, Φ may be based on the angle of rotation of the collimator 24 with respect to the column 16 or the drive assembly 12. Also, the plurality of buttons on the user interface 44 may provide an ability to select various system components and/or directions to be used when determining the angle Φ. By way of example only, the user interface 44 may provide different buttons for requesting movement along each of the Xcart, Ycart, u and v axis.

Returning to the example of FIG. 3, to move in the positive direction of arrow 110, Eqs. 1 and 2 may be used to calculate $V_1$ and $V_2$. $V_t$ may be slower than the magnitude of velocity that is allowed when the system 10 is driven longer distances using the drive handle 38, such as from one room to another. In one embodiment, the magnitude of $V_t$ may be set to a predetermined number such as to achieve a maximum movement, for example, of 100 mm per second or 50 mm per second. It should be understood that the magnitude of $V_t$ may be set to achieve other speeds. In another embodiment, the magnitude of $V_t$ may vary based on the angle of rotation Φ wherein $V_t$ is faster within some predetermined range of Φ. Further, as explained in more detail below, at some angles of Φ, $V_t$ may be zero to prevent movement of the mobile imaging system, regardless of movement of the arm. For example, when Φ is within a predetermined range of angles around zero (e.g., 30 degrees), $V_t$ may be zero to prevent inadvertent movement of the mobile imaging system while the operator is "parking" the arm/imaging assembly (e.g., moving the arm to a position above and between the drive wheels).

When the first and second drive wheels 100 and 102 are driven at different velocities based on the angle of rotation Φ, the drive assembly 12 rotates about an IC located along the drive axis line 112 and the pivot point 108 moves along the u axis (or other selected axis or direction). The operator may disengage the brake on the column 16 as the drive assembly 12 is driven, allowing the column 16 to rotationally "float". The operator may then manually adjust the angle of rotation Φ between the column 16 and the longitudinal axis 118 to either maintain motion along the u axis or change the direction of motion. As the angle of rotation Φ changes, the rotation-based drive module 56 dynamically recalculates the velocities for each of the first and second drive wheels 100 and 102 such that the pivot point 108 continues to move along the u axis or other desired travel direction. As the angle of rotation Φ changes, the drive assembly 12 may rotate about a different IC.

The dynamically changing velocities may be applied to the first and second drive wheels 100 and 102 for a predetermined amount of time, such as five seconds, or a predetermined travel distance, such as 25 mm. Upon expiration of the predetermined amount of time, or upon traveling the predetermined distance, the wheels may be deactivated to stop movement of the mobile imaging system. If the sensors 62, 64 are still outputting signals indicating that the arm is at an end-of-travel position, the wheel(s) may again be activated in the manner described above. In another example, the determined velocities may be applied to the first and second drive wheels 100 and 102 until the signals output by sensors 62, 64 indicate the arm is no longer at an end-of-travel position and/or that the user has stopped the axial movement/force acting on the arm. In a still further example, the determined velocities may be applied to the first and second drive wheels 100 and 102 until the signals output by sensors 62, 64 indicate the user has moved the arm in an opposite direction.

Figure 4:
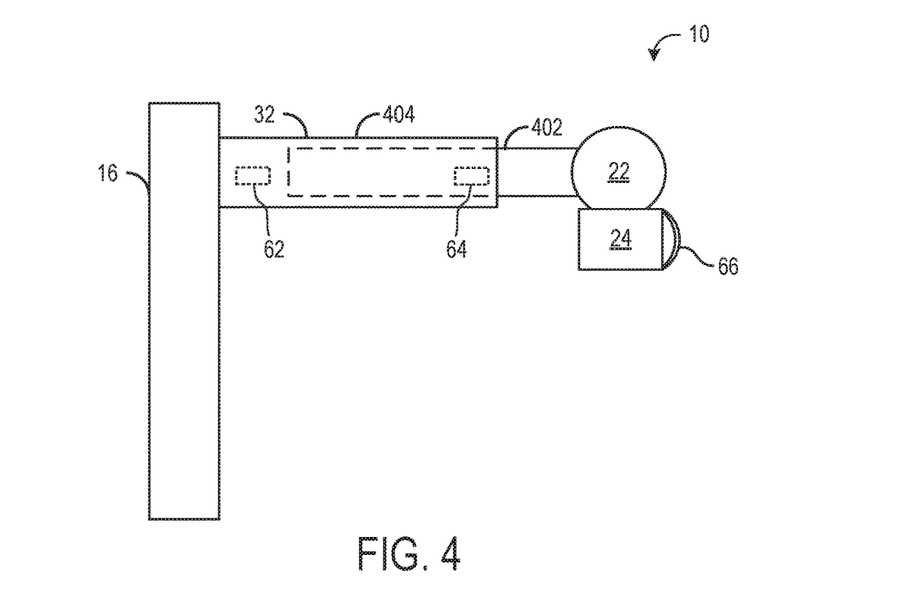
FIG. 4 is a schematic diagram illustrating a telescopic arm and position sensors relative to the column and x-ray tube of the mobile imaging system of FIG. 1.

FIG. 4 shows a schematic side view of portions of the mobile imaging system 10, including column 16, arm 32, x-ray tube housing 22, and collimator 24. As shown in FIG. 4, arm 32 may be comprised of multiple, nested sections to enable a telescoping motion inward toward column 16 and outward away from column 16. As shown, arm 32 includes a first section 402 nestled inside a second section 404, although more than two sections are possible. Push sensor 62 may be positioned on or in arm 32, for example coupled to second section 404, and may be configured to generate signals usable by drive controller 50 to detect when arm 32 has reached a first end-of-travel position, where the first section 402 of arm 32 is unable to continue traveling inward toward column 16. In one non-limiting example, sensor 62 may be an optical sensor configured to detect when a proximate edge (e.g. proximate to column 16) of first section 402 has reached sensor 62 and hence the first end-of-travel position. Pull sensor 64 may be positioned on or in arm 32, for example coupled to first section 402, and may be configured to generate signals usable by drive controller 50 to detect when arm 32 has reached a second end-of-travel position, where the first section 402 of arm 32 is unable to continue traveling outward away from column 16. In one non-limiting example, sensor 64 may be an optical sensor configured to detect when a distal edge (e.g. distal to column 16) of second section 404 has reached sensor 64 and hence the second end-of-travel position.

A second hand-actuatable interface is provided on system 10. The second hand-actuatable interface is shown in FIG. 4 as including a handle 66 coupled to collimator 24. However, the second hand-actuatable interface may take another suitable form, such as one or more knobs, handgrips, shafts, or other component coupled to the imaging assembly and/or arm 32 that may be used to convert user hand/body movement into movement of the arm 32 and associated imaging assembly. Further, the second hand-actuatable interface may not include a separate component, but may instead include an outer surface of the arm 32 and/or a surface or surfaces of the imaging assembly coupled to arm 32 (e.g., an outer surface of x-ray tube housing 22 or outer surface of collimator 24). The second hand-actuatable interface also includes push sensor 62 and pull sensor 64. In this way, user manipulation of a first component of the second hand-actuatable interface (e.g., user manipulation of handle 66) may cause movement of arm 32 either inward toward column 16 (and away from the user) or outward away from column 16 (and toward the user). The resultant movement of arm 32 may be detected by a second component of the second hand-actuatable interface (e.g., push sensor 62 and/or pull sensor 64), and used to trigger drive of one or more of the first and second drive wheels, in order to move column 16, arm 32, and the associated imaging assembly (e.g., x-ray source assembly 15) along the u axis (or other appropriate imaging axis).

In some examples, arm 32 may be fixed in length (e.g., non-telescopic). In such examples, the two position sensors (e.g., sensors 62 and 64) may be replaced by a force sensor(s) that detects the direction the user desires to move the arm, either toward or away from the column 16/pivot point 108. Further, additionally or alternatively, the force that is applied to the arm at the end-of-travel position may be measured, and the measured force may further modify the values of $V_1$ and $V_2$ described above, such that, for example, greater force results in higher velocity values and lesser force results in lower velocity values. Likewise, if sensors 62, 64 output signals indicative of the position/extension of arm 32 as a range of values (e.g., as opposed to merely indicating when the arm is at an end-of-travel position), the degree of penetration into the range of values may be used to modify the values of $V_1$ and $V_2$ such that, for example, greater penetration results in higher velocity and lower penetration results in lower velocity.

In another embodiment, sensor 46 may be replaced with one or more sensors to indicate specific angle ranges. For some angles of Φ, one or more of the first and second drive wheels may be activated to move the mobile imaging system along the u axis (or other suitable axis), and for other angles, the first and second drive wheels would be disabled. This would have the effect of having one or more deadband angles. With this approach, each active angle range may be assigned to a fixed angle of Φ. In a two range example, any active angle of Φ (e.g., any angle outside the deadband range) would equal 180°. This results in both the first and second drive wheels moving at the same velocity regardless of the active Φ angles once the sensors 62, 64 indicate an end-of-travel position has been reached (with output from pull sensor 64 indicating the second end-of-travel position has been reached and hence reverse motion occurring and output from push sensor 62 indicating the first end-of-travel position has been reached and hence forward motion occurring). In this example, the drive wheels would be active until output from the sensors indicate the user is no longer pushing or pulling on the arm. In still further examples, other system inputs such as bumpers, proximity sensors, etc., may interrupt driving of the drive wheels.

In another example, the angle range sensor(s) described above could be configured with four ranges (or other number of ranges) to allow for differential drive between the left and right wheels to have the effect of turning the system. In a still further example, additionally or alternatively, the drive wheels, when driven, may be active for a fixed time or a fixed distance, with a dwell period before reengaging again for a fixed time or distance. In another example, the system may be disabled only by output from the sensors 62, 64 indicating that the arm has been moved a small distance before being moved back to re-enable driving of the drive wheels. Still further, in some examples, a combination of the above-described examples may be used, such as the two angle range example and any other example described herein. To differentiate between the two modes, a user input device, such as a push button switch, may be activated to switch between the two modes. For example, a first mode may include the two angle ranges control described above while a second mode may include the measured angle control (where movement of the wheels is based on the measured angle of rotation of the column without partitioning into ranges).

Thus, the mobile imaging system described above with respect to FIGS. 1-4 includes an imaging assembly (e.g., an x-ray imager) coupled to a mobile drive system and a driving interface configured to move the imaging assembly relative to the mobile drive system both axially and radially in response to user manipulation. The driving interface may be further configured to generate signals in response to the axial movement of the imaging assembly, and the mobile drive system may be configured to move in response to the signals. For example, the imaging assembly may be coupled to the mobile drive system via a rotatable column and a horizontal arm, and the driving interface may include one or more sensors to detect the axial movement of the imaging assembly and generate the signals in response to detecting the axial movement. The driving interface may further include a hand-actuatable component, such as handle 66, where user manipulation (e.g., manual movement) of the hand-actuatable component in a first or second direction moves the imaging assembly axially, and user manipulation of the hand-actuatable component in a third or fourth direction moves the imaging assembly radially. For example, if the handle 66 is moved in a first or second direction along a first axis (e.g., the u axis of FIG. 3), the imaging assembly may move axially along the first axis due to the telescoping nature of the arm 32. If handle 66 is moved in a third or fourth direction (e.g., to the right or left of the first direction, along an arc defined by the pivot point), the imaging assembly may move radially, e.g., rotate about the pivot point due to the rotational coupling of the column 16 to the frame. To prevent free-floating movement of the arm and column, one or more locks and/or brakes may be present on the mobile imaging system. Before moving the arm and imaging assembly via user manipulation, a user may release the one or more locks or brakes. Once the imaging assembly is moved into a desired position, the user may re-engage the one or more locks or brakes to maintain the imaging assembly in the desired position.

When the axial movement of the imaging assembly reaches a first or second end-of-travel position, the signals generated by the one or more sensors may cause a first drive wheel and/or second drive wheel of the mobile drive system to be activated to move the mobile imaging system. The first and/or second drive wheels may be driven at respective velocities that are determined according to the direction of the axial movement and a rotational angle of the rotatable column. In some examples, when the column is within a threshold range of rotational angles, the mobile drive system may be deactivated so that no movement of the first and second drive wheels occurs, even in the presence of the axial movement of the imaging assembly (and even in the presence of the imaging assembly being moved to an end-of-travel position). Further, in some examples, responsive to the user moving the imaging assembly to any position within a range of positions between the first end-of-travel position and the second end-of-travel position, the first drive wheel and second drive wheel may be disabled so that movement of the drive wheels (and hence automated movement of the mobile imaging system) does not occur.

While FIGS. 1-4 are described above with respect to a mobile imaging system including an x-ray imager, other imaging modalities are possible. For example, arm 32 may be coupled to a suitable imaging assembly that includes components of an x-ray imager (as described above), an ultrasound imager, a visible light imager (e.g., camera), or other imaging modality. Further, while differential wheel velocity was described above as being applied to cause the mobile imaging system to turn, other mechanisms are possible, such as an automatic steering system to adjust the angle of the drive wheels relative to the frame of the mobile imaging system to turn the mobile imaging system, where the angle is adjusted based on the degree of rotation of the column, for example.

Figure 5:
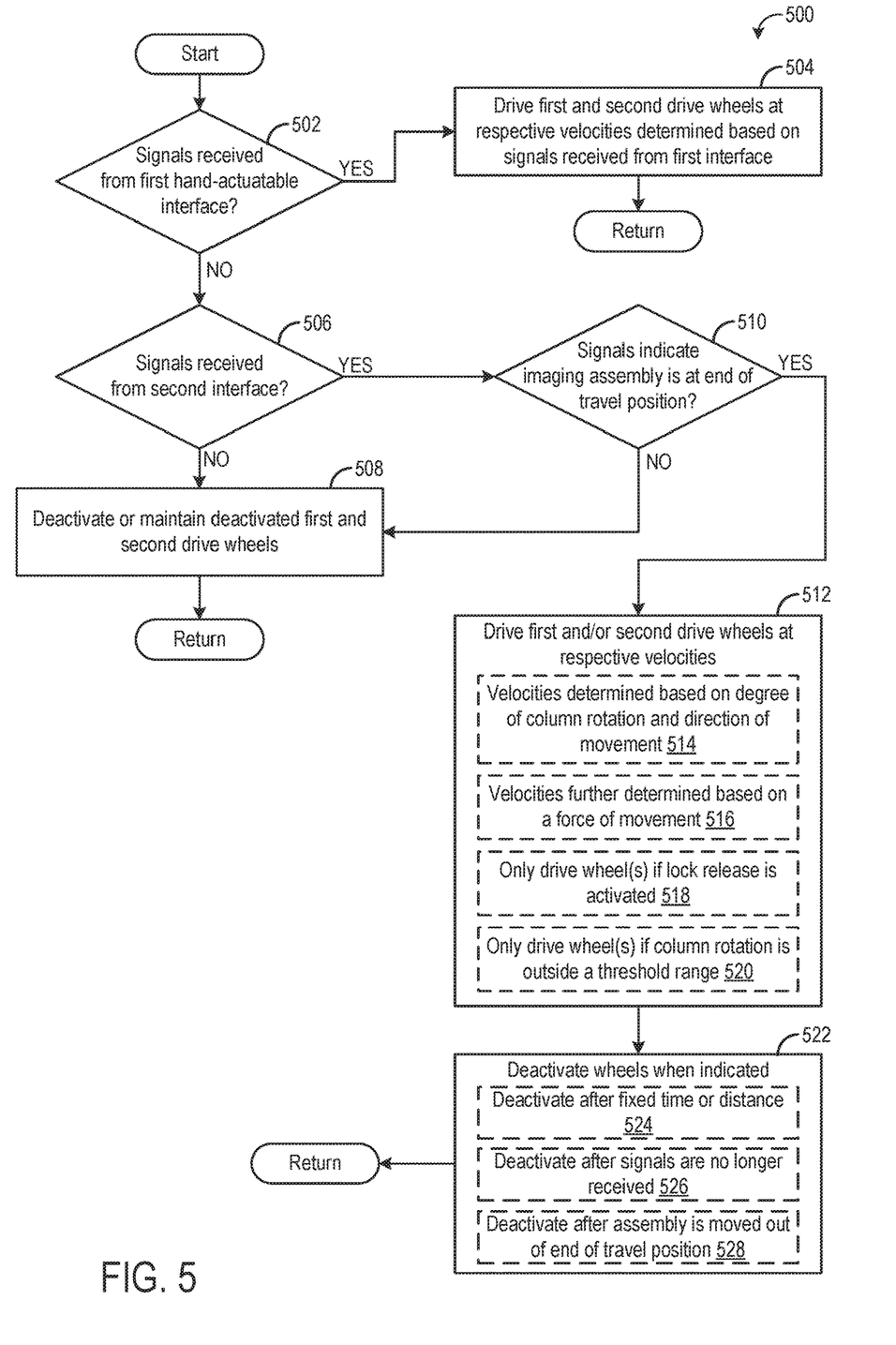
FIG. 5 is a flow chart illustrating an example method for driving a mobile imaging system.

FIG. 5 is a flowchart illustrating a method 500 for controlling movement of a mobile imaging system, such as mobile imaging system 10. Instructions for carrying out method 500 and the rest of the methods included herein may be executed by a controller (e.g., drive controller 50 shown in FIG. 1) based on instructions stored on a memory of the controller and in conjunction with signals received from sensors of the mobile imaging system, such as the sensors described above with reference to FIGS. 1-4. The controller may employ actuators of the mobile imaging system (e.g., the first and second drive wheels, which may be driven by one or more electric motors) to move the mobile imaging system, according to the methods described below.

At 502, method 500 includes determining if signals are received from a first hand-actuatable interface. As explained above with respect to FIG. 1, the mobile imaging system may include a first hand-actuatable interface (e.g., drive handle 38) that outputs signals to drive controller 50 indicative of a desired direction of movement of the mobile imaging system. In response to the signals, the drive controller may activate one or more drive wheels, such as first drive wheel 100 and/or second drive wheel 102, in order to move the mobile imaging system. Accordingly, if signals are received from the first hand-actuatable interface (e.g., if a user is manipulating the drive handle 38), method 500 proceeds to 504 to drive the first and second drive wheels at respective velocities determined based on the received signals. For example, the first and second drive wheels may be driven at the same velocity to move the mobile imaging system in a straight line (whether or forward or reverse), or the first and second drive wheels may be driven at different velocities in order to radially move the mobile imaging system (e.g., turn the mobile imaging system). Method 500 then returns. However, in some examples, if signals are received from the first hand-actuatable interface and signals are concurrently received from a second interface (which is described below and may include a hand-actuatable component coupled to the imaging assembly and/or arm and the sensors 62, 64), the signals received from the second interface may be given priority, such that the signals from the first hand-actuatable interface are ignored and the first and second drive wheels are moved according to the signals received from the second interface. In still further examples, if signals are received from the first hand-actuatable interface and signals are concurrently received from the second interface, the signals may cancel each other out and no movement of the first and second drive wheels may occur.

If signals are not received from the first hand-actuatable interface (e.g., a user is not manipulating the drive handle), method 500 proceeds to 506 to determine if signals are received from the second interface. As described above with respect to FIG. 4, the second interface may include a first hand-actuatable component to translate user movement into movement of the arm and/or column of the mobile imaging system, as well as one or more sensors to detect movement of the arm of the mobile imaging system (and associated imaging assembly) relative to the column of the mobile imaging system. If signals are not received from the second interface (e.g., if signals are not received from the one or more sensors of the second interface), method 500 proceeds to 508 to deactivate or maintain deactivated the first and second drive wheels. Because signals are not received from the first or second interfaces, no automated or controlled movement of the mobile imaging system is indicated. However, manual movement of various components of the mobile imaging system may still occur, such as rotational movement of the column and/or movement of the arm between a first end-of-travel position and a second end-of-travel position. Method 500 then returns.

If signals are received from the second interface (e.g., if one or more of sensor 62 and sensor 64 indicates the arm is moving and/or has reached an end-of-travel position), method 500 proceeds to 510 to determine if the signals indicate the imaging assembly/arm is at an end-of-travel position. As explained above with respect to FIG. 4, the arm on which the imaging assembly is mounted may be configured to move (via user manipulation) between a first end-of-travel position (e.g., where the arm is fully retracted) and a second end-of-travel position (where the arm is fully extended), and the sensors of the second interface may generate signals that are sent to the drive controller and are usable by the drive controller to determine if the arm/imaging assembly is at an end-of-travel position, and if so, which end-of-travel position. Further, the sensors may additionally generate signals usable by the drive controller to determine a force applied by the user during movement of the arm/imaging assembly, and/or a position of the arm (relative to the end-of-travel positions). However, in some examples, the sensors may be configured to only output signals indicating the position of the arm when the arm has reached an end-of-travel position. For example, if the arm is moving between the end-of-travel positions, the sensors may not output any signals. Once the arm reaches an end-of-travel position, one or more of the sensors may then generate signals indicating that the arm is at an end-of-travel position. In still further examples where the arm is of a fixed length, the sensor(s) of the second interface may output signals when a user moves the imaging assembly/arm axially, as the imaging assembly/arm may always be at an "end-of-travel" position and thus the determination may be based on the axial movement (or based on axial force applied by the user, as the imaging assembly may not necessarily move in response to the manual input).

If the signals from the second interface sensors do not indicate the imaging assembly is at an end-of-travel position, for example if the signals indicate that the arm is being moved between the end-of-travel positions, method 500 proceeds to 508 to deactivate or maintain deactivated the first and second drive wheels, and then method 500 returns. However, in some examples, if signals are received from the sensor(s) of the second interface that indicate the arm/imaging assembly is being moved, but is not at an end-of-travel position, the drive controller may be configured to drive the first and/or second drive wheels based on the position of the arm.

If the signals from the second interface sensors do indicate the imaging assembly is at an end-of-travel position, method 500 proceeds to 512 to drive the first and/or second drive wheels at respective velocities. In some examples, such as examples where the arm is a fixed length, the arm/imaging assembly may always be at an "end-of-travel" position, but the actual determination that the user intends the arm/imaging assembly to be at the end-of-travel position may be based on the force sensor (present in such an example) outputting signals indicating the user is imparting an axial motion on the hand-actuatable component of the second interface either toward or away from the column. The first and/or second drive wheels may be driven by activating an electric motor(s) (which may be a common electric motor for both wheels or a respective electric motor in examples where each drive wheel is driven by a separate motor) coupled to the first and/or second drive wheels, thereby causing the drive wheel(s) to rotate in a forward or reverse direction at a commanded respective velocity. For example, the first drive wheel may be driven by first motor 101 of FIG. 2 and the second drive wheel may be driven by second motor 103 of FIG. 2.

Driving the first and/or second drive wheels at respective velocities may include, as indicated at 514, driving the first and/or second drive wheels at respective velocities determined based on a degree of rotation of the column of the mobile imaging system and a direction of movement of the arm/imaging assembly (or direction of force applied to the arm/imaging assembly via the hand-actuatable component). For example, the drive controller may determine, based on the received signals, whether the arm was moved to the first end-of-travel position (where the user imparted a push input on the arm/imaging assembly to move the arm/imaging assembly toward the column and away from the user until the first end-of-travel position was reached) or to the second end-of-travel position (where the user imparted a pull input on the arm/imaging assembly to move the arm/imaging assembly away from the column and toward the user until the second end-of-travel position was reached). If the sensor that measures the rotation of the column (e.g., sensor 46) is outputting signals indicating that the column has been swiveled to 180° (such that the imaging assembly is positioned over the front of the frame of the mobile imaging system), and if the signals from the arm position sensors (e.g., 62 and 64) indicate the arm/imaging assembly was moved to the first end-of-travel position, the first and/or second drive wheels may be driven in a reverse direction, for example, to move the mobile imaging system in reverse and away from the user. If the signals indicate that the column is at 180° and the arm/imaging assembly is moved to the second end-of-travel position, the first and/or second drive wheels may be driven in a forward direction, for example, to move the mobile imaging system forward and toward the user.

Additionally, in order to move the imaging assembly along a desired axis, regardless of where the imaging assembly is positioned relative to the frame of the mobile imaging system (e.g., due to rotational movement of the imaging assembly around the pivot point of the column), the first and/or second drive wheels may be driven at respective velocities that are determined based on the angle of rotation of the column. The velocities may be determined according to Eqs. 1-4 as described above, or other suitable velocity equations. Depending on the angle of rotation of the column, both of the first and second drive wheels may be driven, or only one of the drive wheels may be driven. Further, depending on the angle of rotation of the column, the first and second drive wheels may be driven at the same velocity, or they may be driven at different velocities. Further still, depending on the angle of rotation of the column, the first and second drive wheels may be driven in the same direction, or they may be driven in different directions.

For example, when the output from the sensors of the second interface indicate the operator desires to move the imaging assembly toward the pivot point 108 (e.g., away from the operator), the drive controller determines the velocity of the first drive wheel based on Eq. 3 and the velocity of the second drive wheel based on Eq. 4:

$$V_1=-(b*V_t*\sin\Phi/2R-V_t*\cos\Phi) \quad \text{Eq. 3}$$

$$V_2=-(-b*V_t*\sin\Phi/2R-V_t*\cos\Phi) \quad \text{Eq. 4}$$

In Eqs. 3 and 4, R is the distance between the pivot point and a center point along drive axis (e.g. line 112 of FIG. 3) between the first and second drive wheels, b is the distance between the first and second drive wheels, and $V_t$ is the desired magnitude of the velocity of the imaging assembly. If R is 600 mm, b is 300 mm, $V_t$ is 100 mm/sec, and $\Phi$ is 60°, $V_1$ may be 28 mm/sec and $V_2$ may be 72 mm/sec, while if $\Phi$ is 90°, $V_1$ may be −25 mm/sec and $V_2$ may be 25 mm/sec.

Figure 6:
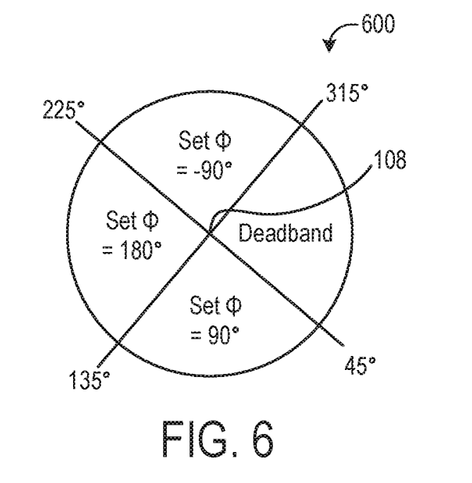
FIGS. 6-7 are graphs schematically illustrating example angle ranges for set movement of the mobile imaging system.

However, in some examples, such as those explained above, the actual angle of rotation of the column is not entered into the equation, but rather a set angle within a range of angles is entered. For example, referring to FIG. 6, a first example 600 set of ranges of angles is schematically shown. The first example 600 includes four ranges of angles. A first range (315-45°) shown in first example 600 is a deadband range where no movement of the drive wheels occurs (e.g., any angle in the first range results in $V_1$ and $V_2$ each being zero). In a second range (45-135°), all angles within the second range are set to 90°, in a third range (135-225°), all angles within the third range are set to 180°, and in a fourth range (225-315°), all angles within the fourth range are set to −90°. In such an example, $V_1$ may be −25 mm/sec and $V_2$ may be 25 mm/sec when $\Phi$ is both 60° and 90°. In examples where the wheels move at the same speed, but in opposite directions, the mobile imaging system may rotate about the center point between the two wheels.

Figure 7:
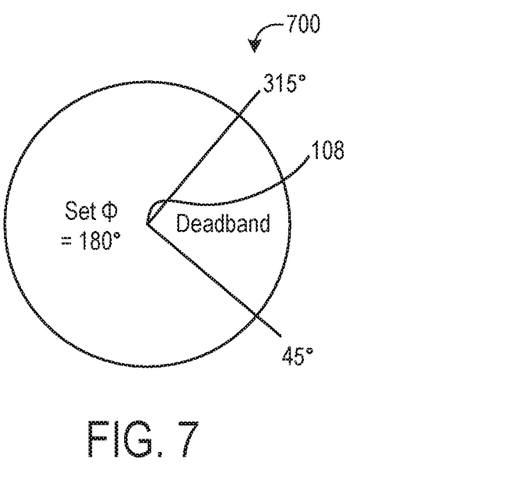

FIG. 7 shows a second example 700 set of ranges, where the deadband range is between 315-45° and all other angles are set to 180°. In this example, the mobile imaging system is either not moved at all, or moved at a predetermined speed and direction (e.g., $V_1$ and $V_2$ may each be −100 mm/sec when the column is moved out of the deadband range, if R, b, and $V_t$ are set as above).

Driving the first and/or second drive wheels at respective velocities may additionally or alternatively include, as indicated at 516, driving the first and/or second drive wheels at respective velocities determined based on a force of movement of the arm at the end-of-travel position. For example, the first and/or second drive wheels may be driven at respective velocities that are proportional to the force applied by the user when moving the arm/imaging assembly, such that the wheels may be driven at higher velocities when greater force is applied, and lower velocities when lower force is applied.

Further, additionally or alternatively, driving the first and/or second drive wheels may include, as indicated at 518, only driving the first and/or second drive wheels if a lock release is activated or actuated. For example, the mobile imaging system may include one or more locking mechanisms that impede or prevent movement of the mobile imaging system in response to manipulation of the second hand-actuatable interface, and the locking mechanism(s) may include a lock release that, once released, allows the axial movement of the arm/imaging assembly (via the second hand-actuatable interface) to result in driving of the first and/or second drive wheels (release of the lock or brake may also allow for radial movement of the arm/imaging assembly). Further still, additionally or alternatively, driving the first and/or second drive wheels may include, as indicated at 520, only driving the first and/or second drive wheels if the degree of rotation of the column is outside a threshold range of rotation. For example, the degree of rotation of the column may be defined relative to the longitudinal axis of the mobile imaging system frame and an imaging assembly axis, where the imaging assembly axis corresponds to the axis that passes through the pivot point of the column and the imaging assembly (e.g., the u axis of FIG. 3). For example, when the imaging assembly axis is parallel to the longitudinal axis and the imaging assembly is positioned intermediate/over the drive wheels, the degree of rotation of the column may be zero degrees and the imaging assembly may be considered to be in a parked position. Driving of the first and second drive wheels in response to axial movement of the arm/imaging assembly may be prevented when the column is within a threshold range of the parked position, such as within 30 or 45 degrees of the parked position. Such a configuration may prevent unintended movement of the mobile imaging system while the operator is attempting to "park" the imaging assembly, e.g., position the imaging assembly back in a home position, which may be a transport position where the imaging assembly is locked in place so the assembly does move while the mobile imaging system is moved via the first hand-actuatable interface.

At 522, method 500 includes deactivating the first and/or second drive wheels when indicated. The driven wheels (whether one or both of the first and second drive wheels) may be deactivated by stopping the electric motor(s). The wheel(s) may be deactivated after a fixed time or a fixed distance, as indicated at 524. For example, once the first and/or second drive wheels are activated, the wheel(s) may be driven for a predetermined time (e.g., one second) or predetermined distance (e.g., 5 cm) and then the wheels may be deactivated until another input moving the arm/imaging assembly to an end-of-travel distance is identified. In other example, as indicated at 526, the driven wheel(s) may be deactivated after the signals from the sensor(s) of the second interface are no longer received (e.g., the user stops pushing or pulling on the hand-actuatable component of the second interface). In a still further example, the driven wheel(s) may be deactivated after the imaging assembly/arm is moved out of the end-of-travel position, as indicated at 528. For example, once the user decides to stop movement of the mobile imaging system, the user may cease the axial movement at the end-of-travel position and may instead move the hand-actuatable component of the second interface in an opposite direction, at least temporarily, to stop movement of the drive wheels. Method 500 then returns.

Figure 8:
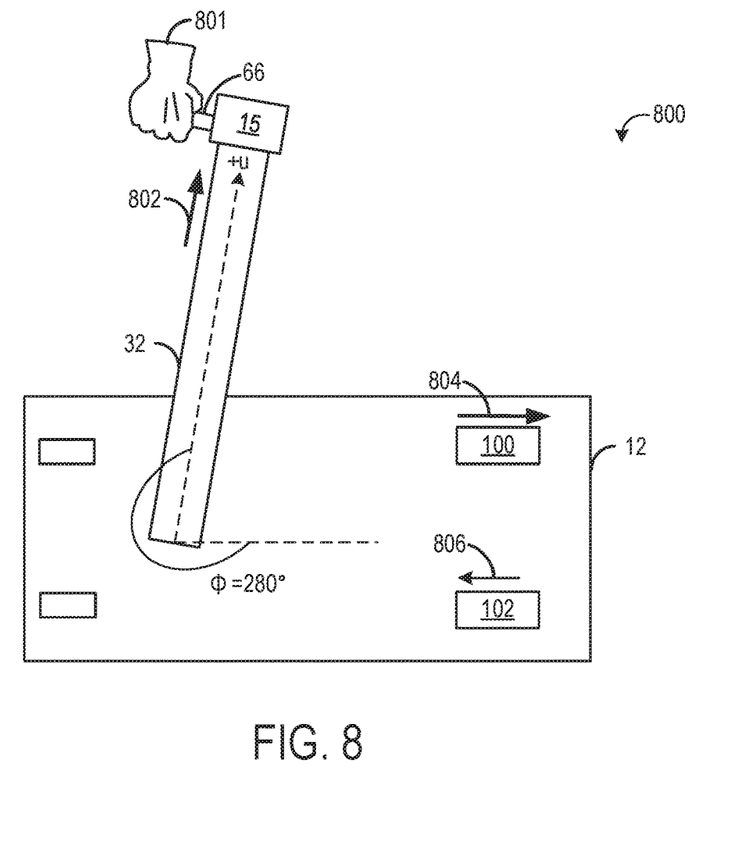
FIGS. 8-9 schematically show example movement of the mobile imaging system.

FIG. 8 schematically shows example movement 800 of the mobile imaging system 10 according to first user manipulation of a hand-actuatable component of the second interface, and according to signals generated by the position sensors (e.g., sensors 62 and 64) of the second interface. FIG. 8 includes a schematic of a hand 801 of a user providing input to handle 66 (herein shown as being coupled to x-ray source housing 15 for visual purposes, but the handle may be positioned elsewhere, such as coupled to the collimator as described above). The user manipulation has moved the column to a first degree of rotation, $\Phi=280°$. The user manipulation has also moved arm 32 to an end-of-travel position (e.g., the second end-of-travel position where the arm is fully extended) with a force of movement 802, in a direction away from the column and toward the user. The drive controller receives the signals from the sensors and in response determines velocities for driving the first drive wheel 100 and second drive wheel 102 based on the degree of rotation of the column and also based on the force of movement of the arm/imaging assembly. Because the movement of the arm is away from the pivot point of the column, the drive controller may use Eqs. 1 and 2, described above, to determine that the first velocity for the first drive wheel, $V_1$, is −42 mm/sec (assuming b, R, and $V_t$ are the same as described above) and that the second velocity for the second drive wheel, $V_2$, is 7 mm/sec. Thus, the first drive wheel 100 may be driven in a first direction at a first, higher magnitude of velocity 804, while the second drive wheel 102 may be driven in a second direction at a second, lower magnitude of velocity 806, where the second velocity is lower than the first velocity. Because the second velocity is different than the first velocity, the motorized drive assembly 12 may not travel straight, but instead may turn, in order to move the imaging assembly in a straight line along the imaging axis (e.g., the u axis of FIG. 8).

Figure 9:
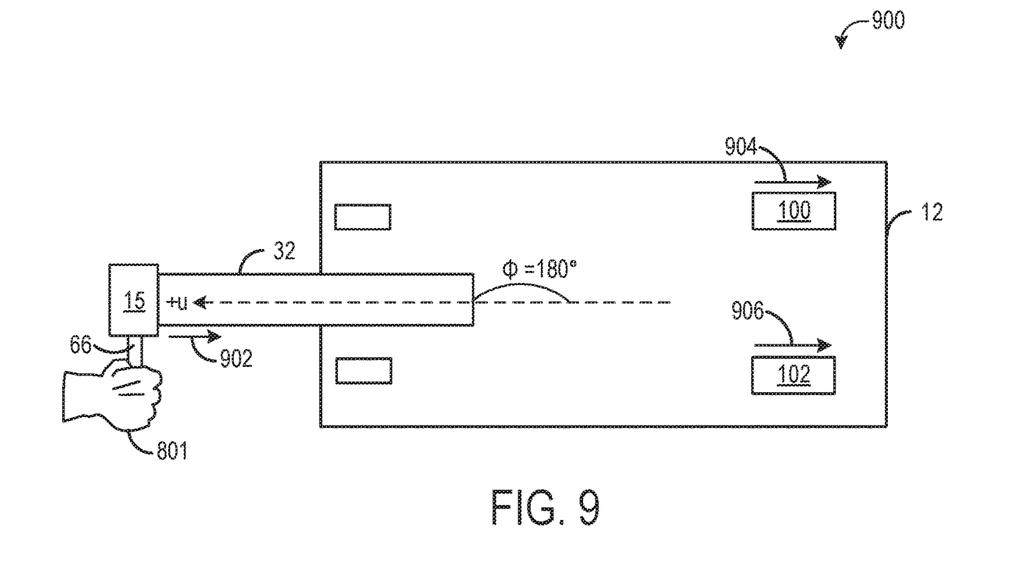

FIG. 9 schematically shows example movement 900 of the mobile imaging system 10 according to second user manipulation of the handle. In FIG. 9, the hand 801 of the user has manipulated the handle to move the column to a second degree of rotation, $\Phi=180°$. The user has also manipulated the handle to move arm 32 to an end-of-travel position (e.g., the first end-of-travel position where the arm is fully retracted) with a force of movement 902, in a direction toward the column and away from the user. The drive controller receives the signals from the sensors and in response determines velocities for driving the first drive wheel 100 and second drive wheel 102 based on the degree of rotation of the column. Because the movement of the arm is toward the pivot point of the column, the drive controller may use Eqs. 3 and 4, described above, to determine that the first velocity for the first drive wheel, $V_1$, is −100 mm/sec (assuming b, R, and $V_t$ are the same as described above) and that the second velocity for the second drive wheel, $V_2$, is −100 mm/sec. Thus, the first drive wheel 100 may be driven in a second direction at a third velocity 904, while the second drive wheel 102 may be driven in the second direction at a fourth velocity 906, where the third velocity is equal to the fourth velocity. It is to be understood that the example velocities and force scaling provided herein are exemplary, and other velocities are possible.

In some examples, the mobile imaging system may include a force sensor to measure an amount of force applied by the user when rotating the column and/or moving the arm. When a force sensor is included, the velocities of the drive wheels may be adjusted based on the detected amount of force. For example, there may be a threshold force (such as zero) above which the movement of the arm would initiate at a minimum magnitude of $V_t$ and then increase from there up to a maximum value of $V_t$. Using the above FIGS. 8 and 9 as examples, the force applied in FIG. 9 may be relatively small, so $V_t$ used to calculate the velocities $V_1$ and $V_2$ may be scaled to a minimum $V_t$ (e.g., 50 mm/sec), and as the force applied by the user increases, $V_t$ may increase towards a maximum value. The force applied in FIG. 8 may be relatively large, so $V_t$ used to calculate the velocities $V_1$ and $V_2$ may be scaled to a maximum $V_t$ (e.g., 200 mm/sec).

A technical effect of a mobile imaging system including a driving interface configured to move an imaging assembly relative to a mobile drive system both axially and radially in response to user manipulation, and further configured to generate signals in response to the axial movement of the imaging assembly, the mobile drive system configured to move in response to the signals, is automated movement of the mobile drive system in an intuitive manner that does not require a separate input to a user interface.

An example provides for a mobile imaging system, including a mobile drive system, an imaging assembly coupled to the mobile drive system, and a driving interface configured to move the imaging assembly relative to the mobile drive system both axially and radially in response to user manipulation, and further configured to generate signals in response to the axial movement of the imaging assembly, the mobile drive system configured to move in response to the signals. In a first example of the system, the imaging assembly is coupled to the mobile drive system via a rotatable column and a horizontal arm, and the driving interface comprises one or more sensors to detect the axial movement of the imaging assembly and generate the signals in response to detecting the axial movement. In a second example of the system, which optionally includes the first example, the driving interface further comprises a hand-actuatable component, wherein user manipulation of the hand-actuatable component in a first or second direction moves the imaging assembly axially, and wherein user manipulation of the hand-actuatable component in a third or fourth direction moves the imaging assembly radially. In a third example of the system, which optionally includes one or both of the first and second examples, the mobile drive system includes a first drive wheel and a second drive wheel, and wherein the mobile drive system is configured to move by one or more of the first drive wheel being driven by a first motor and the second drive wheel being driven by a second motor. In a fourth example of the system, which optionally includes one or more or each of the first through third examples, the mobile drive system includes a controller storing instructions in non-transitory memory executable by the controller to activate the first motor to drive the first drive wheel at a first drive velocity and/or activate the second motor to drive the second drive wheel at a second drive velocity, the first and second drive velocities determined based on an angle of rotation of the column relative to a longitudinal axis of the mobile drive system and based on the axial movement of the imaging assembly. In a fifth example of the system, which optionally includes one or more or each of the first through fourth examples, the first and second velocities are further based on a force of the axial movement of the imaging assembly. In a sixth example of the system, which optionally includes one or more or each of the first through fifth examples, the instructions are executable to activate the first motor to drive the first drive wheel at the first drive velocity and/or activate the second motor to drive the second drive wheel at the second drive velocity in response to the signals generated by the one or more sensors, and wherein the signals are only generated in response to the axial movement bringing the imaging assembly to an end-of-travel position. In a seventh example of the system, which optionally includes one or more or each of the first through sixth examples, the method further includes a lock release configured to, when activated, disengage one or more brakes or locks of the mobile drive system, and wherein the instructions are executable to move the mobile drive assembly in response to the signals only if a user has activated the lock release. In an eighth example of the system, which optionally includes one or more or each of the first through seventh examples, the hand-actuatable component is a first hand-actuatable component and the signals are first signals, and further comprising a second hand-actuatable component coupled to the mobile drive system, and wherein the instructions are executable to activate one or more of the first and second drive wheels to move the mobile imaging system responsive to second signals received from the second hand-actuatable component, the second signals generated in response to user manipulation of the second hand-actuatable component. In a ninth example of the system, which optionally includes one or more or each of the first through eighth examples, the instructions are executable to, when the column is within a threshold range of rotational angles, deactivate the mobile drive system, even in the presence of the axial movement of the imaging assembly.

An example provides for a method for a mobile imaging system including a radiation source coupled to a frame via a rotatable column and an arm, the method including, responsive to a the radiation source being positioned at an end-of-travel position and a force being applied to the radiation source along an axis of the radiation source, driving one or more of a first drive wheel and a second drive wheel of the mobile imaging system at respective velocities determined based on a degree of rotation of the rotatable column and a direction of the force. In a first example of the method, the end-of-travel position is a first end-of-travel position located proximate the column, and driving one or more of the first drive wheel and the second drive wheel of the mobile imaging system comprises driving one or more of the first drive wheel and the second drive wheel of the mobile imaging system to move the mobile imaging system in a first direction away from the user. In a second example of the method, which optionally includes the first example, the end-of-travel position is a second end-of-travel position located distal to the column, and wherein driving one or more of the first drive wheel and the second drive wheel of the mobile imaging system comprises driving one or more of the first drive wheel and the second drive wheel of the mobile imaging system to move the mobile imaging system in a second direction toward the user. In a third example of the method, which optionally includes one or both of the first and second examples, the end-of-travel position is a first end-of-travel position, wherein the radiation source is movable along an axis from the first end-of-travel position to a second end-of-travel position, and further comprising responsive to the user moving the radiation source to any position within a range of positions between the first end-of-travel position and the second end-of-travel position, disabling the first drive wheel and second drive wheel.

An example provides for a mobile imaging system including a first hand-actuatable driving interface, an imaging assembly, a mobile drive system coupled to the imaging assembly and configured to drive the imaging system responsive to user manipulation of the first hand-actuatable driving interface, and a second driving interface coupled to a first moveable component of the mobile drive system including a hand-actuatable component, the mobile drive system further configured to move based on a degree of motion of the first movable component. In a first example of the system, the first movable component of the mobile drive system comprises an arm coupled to a rotatable column, the column coupled to and extending up from a frame of the mobile drive system, the arm further coupled to the imaging assembly. In a second example of the system, which optionally includes the first example, the arm is a telescoping arm configured to telescope toward the column in response to a push input on the hand-actuatable component of the second driving interface and to telescope away from the column in response to a pull input on the hand-actuatable component of the second driving interface, and the column is configured to rotate around a pivot point of the mobile drive system in response to rotational input on the hand-actuatable component of the second driving interface. In a third example of the system, which optionally includes one or both of the first and second examples, the second driving interface comprises one or more sensors configured to detect the degree of motion of the arm. In a fourth example of the system, which optionally includes one or more or each of the first through third examples, the mobile drive system comprises a controller storing instructions in non-transitory memory executable by the controller to: determine the degree of motion of the arm based on output from the one or more sensors; responsive to the degree of relative motion reaching a first threshold value, drive one or more wheels of the mobile drive system to move the mobile drive system in a first direction; and responsive to the degree of motion reaching a second threshold value, different than the first threshold value, drive one or more wheels of the mobile drive system to move the mobile drive system in a second direction. In a fifth example of the system, which optionally includes one or more or each of the first through fourth examples, the instructions are further executable to, responsive to the degree of motion being between the first threshold value and the second threshold value, not drive the one or more wheels of the mobile drive system.

In another representation, a mobile imaging system includes a mobile drive system, a column coupled to the mobile drive system, a radiation source coupled to the column via a horizontal arm, the arm having a range of motion along an axis between a proximate end position and a distal end position, and a controller storing instructions in non-transitory memory executable by the controller to, responsive to the arm being moved to the proximate end position or the distal end position, engage the mobile drive system to move the mobile imaging system, thereby moving the radiation source along the axis. In a first example of the system, the mobile drive system includes a first drive wheel and a second drive wheel, and wherein engaging the mobile drive system comprises driving the first drive wheel at a first drive velocity and driving the second drive wheel at a second drive velocity. In a second example of the system, which optionally includes the first example, the column is rotatable relative to the mobile drive system, and the first and second drive velocities are determined based on an angle of rotation of the column relative to a longitudinal axis of the mobile drive system and based on whether the arm is moved to the proximate end position or the distal end position. In a third example of the system, which optionally includes one or both of the first and second examples, the first and second velocities are further based on a force of movement of the arm when the arm is moved to the proximate end position or the distal end position. In a fourth example of the system, which optionally includes one or more or each of the first through third examples, the system further includes a first sensor positioned on the arm proximate the column and a second sensor positioned on the arm proximate the radiation source. In a fifth example of the system, which optionally includes one or more or each of the first through fourth examples, the instructions are executable to determine if the arm has been moved to the proximate position responsive to output from the first sensor and determine if the arm has been moved the distal position responsive to output from the second sensor. In a sixth example of the system, which optionally includes one or more or each of the first through fifth examples, the system further includes a lock release configured to, when activated, disengage one or more brakes or locks of the mobile drive system, and wherein the instructions are executable to obtain output from the first and second sensors responsive to a user activating the lock release. In a seventh example of the system, which optionally includes one or more or each of the first through sixth examples, the system further includes a drive handle, and wherein the instructions are executable to engage the mobile drive system to move the mobile imaging system responsive to signals received from the drive handle, the signals generated in response to manipulation of the drive handle by a user. In an eighth example of the system, which optionally includes one or more or each of the first through seventh examples, the instructions are executable to, when the column is within a threshold range of angles of rotation of the column relative to a longitudinal axis of the mobile drive system, disengage the mobile drive system, even if the arm is moved to the proximate end position or the distal end position. In a ninth example of the system, which optionally includes one or more or each of the first through eighth examples, the system further includes a drive handle, and wherein the instructions are executable to over-ride the disengagement of the mobile drive system and engage the mobile drive system to move the mobile imaging system responsive to signals received from the drive handle, the signals generated in response to manipulation of the drive handle by a user.

In another representation, a method for a mobile imaging system including a radiation source coupled to a frame via a rotatable column and an arm includes responsive to a user moving the radiation source to an end-of-travel position, driving one or more of a first drive wheel and a second drive wheel of the mobile imaging system at respective velocities determined based on a degree of rotation of the rotatable column and a direction of the movement of the radiation source.

In another representation, a mobile imaging system includes a mobile drive system including a frame, a first drive wheel coupled to the frame, and a second drive wheel coupled to the frame; a drive handle coupled to the frame; a column rotatably coupled to the frame and configured to rotate about a rotation axis in response to manipulation by a user; a radiation source coupled to the column via a horizontal arm, the radiation source configured to move along a radiation source axis between a proximate end position and a distal end position in response to manipulation by the user; and a controller storing instructions in non-transitory memory executable by the controller to: responsive to signals received from the drive handle, move the mobile imaging system by driving the first drive wheel at a first velocity and driving the second drive wheel at a second velocity, the signals generated in response to manipulation of the drive handle by a user; and responsive to the radiation source being moved by the user to the proximate end position or the distal end position, automatically move the radiation source along the radiation source axis by driving the first drive wheel at a third velocity and driving the second drive wheel at a fourth velocity. In a first example of the system, the instructions are executable to move the radiation source along the radiation source axis only in response to the radiation source being moved to the proximate end position or the distal end position and not when the radiation source is moved by the user to any other position between the proximate end position or the distal end position. In a second example of the system, which optionally includes the first example, the instructions are executable to terminate the automatic movement of the radiation source along the radiation source axis by deactivating the first drive wheel and the second drive wheel after a fixed duration or a fixed distance. In a third example of the system, which optionally includes one or both of the first and second examples, the instructions are executable to terminate the automatic movement of the radiation source along the radiation source axis responsive to the arm being moved in an opposite direction from a direction of the movement.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A mobile imaging system, comprising:
   a mobile drive system;
   an imaging assembly coupled to the mobile drive system; and
   a driving interface configured to move the imaging assembly relative to the mobile drive system both axially and radially in response to user manipulation, and further configured to generate signals only in response to the axial movement of the imaging assembly bringing the imaging assembly to an end-of-travel position, the mobile drive system configured to move in response to the signals.

2. The mobile imaging system of claim 1, wherein the imaging assembly is coupled to the mobile drive system via a rotatable column and a horizontal arm, wherein the driving interface comprises one or more sensors to detect the axial movement of the imaging assembly and generate the signals in response to detecting the axial movement, and wherein the signals to move the mobile drive system are further based on a force of the axial movement of the imaging assembly.

3. The mobile imaging system of claim 2, wherein the driving interface further comprises a hand-actuatable component, wherein user manipulation of the hand-actuatable component in a first or second direction moves the imaging assembly axially, and wherein user manipulation of the hand-actuatable component in a third or fourth direction moves the imaging assembly radially.

4. The mobile imaging system of claim 2, wherein the mobile drive system includes a first drive wheel and a second drive wheel, and wherein the mobile drive system is configured to move by one or more of the first drive wheel being driven by a first motor and the second drive wheel being driven by a second motor.

5. The mobile imaging system of claim 4, wherein the mobile drive system includes a controller storing instructions in non-transitory memory executable by the controller to activate the first motor to drive the first drive wheel at a first drive velocity and/or activate the second motor to drive the second drive wheel at a second drive velocity, the first and second drive velocities determined based on an angle of rotation of the column relative to a longitudinal axis of the mobile drive system and based on the axial movement of the imaging assembly.

6. The mobile imaging system of claim 5, wherein the first and second velocities are further based on the force of the axial movement of the imaging assembly, and wherein the first and/or second drive wheels are driven until the imaging assembly is no longer at the end-of-travel position and/or the axial movement ceases.

7. The mobile imaging system of claim 5, wherein the instructions are executable to activate the first motor to drive the first drive wheel at the first drive velocity and/or activate the second motor to drive the second drive wheel at the second drive velocity in response to the signals generated by the one or more sensors.

8. The mobile imaging system of claim 5, further comprising a lock release configured to, when activated, disengage one or more brakes or locks of the mobile drive system, and wherein the instructions are executable to move the mobile drive assembly in response to the signals only if a user has activated the lock release.

9. The mobile imaging system of claim 5, wherein the hand-actuatable component is a first hand-actuatable component and the signals are first signals, and further comprising a second hand-actuatable component coupled to the mobile drive system, and wherein the instructions are executable to activate one or more of the first and second drive wheels to move the mobile imaging system responsive to second signals received from the second hand-actuatable component, the second signals generated in response to user manipulation of the second hand-actuatable component.

10. The mobile imaging system of claim 5, wherein the instructions are executable to, when the column is within a threshold range of rotational angles, deactivate the mobile drive system, even in the presence of the axial movement of the imaging assembly.

11. A method for a mobile imaging system including a radiation source coupled to a frame via a rotatable column and an arm, the method comprising:
    responsive to the radiation source being positioned at an end-of-travel position and a force being applied to the radiation source along an axis of the radiation source, driving one or more of a first drive wheel and a second drive wheel of the mobile imaging system at respective velocities determined based on a degree of rotation of the rotatable column and a direction of the force, the end-of-travel position including a position where the radiation source is prevented from further movement in the direction of the force along the axis of the radiation source.

12. The method of claim 11, wherein the end-of-travel position is a first end-of-travel position located proximate the column, and wherein driving one or more of the first drive wheel and the second drive wheel of the mobile imaging system comprises driving one or more of the first drive wheel and the second drive wheel of the mobile imaging system to move the mobile imaging system in a first direction away from the user.

13. The method of claim 11, wherein the end-of-travel position is a second end-of-travel position located distal to the column, and wherein driving one or more of the first drive wheel and the second drive wheel of the mobile imaging system comprises driving one or more of the first drive wheel and the second drive wheel of the mobile imaging system to move the mobile imaging system in a second direction toward the user.

14. The method of claim 11, wherein the end-of-travel position is a first end-of-travel position, wherein the radiation source is movable along the axis from the first end-of-travel position to a second end-of-travel position, and further comprising responsive to the user moving the radiation source to any position within a range of positions between the first end-of-travel position and the second end-of-travel position, disabling the first drive wheel and second drive wheel.

15. A mobile imaging system, comprising:
    an imaging assembly;
    a mobile drive system coupled to the imaging assembly and configured to drive the imaging system responsive to user manipulation of a first hand-actuatable driving interface coupled to the mobile drive system; and a second driving interface including a hand-actuatable component positioned on or forming a part of a first movable component of the mobile drive system, the first movable component including an imaging assembly or an arm coupling the imaging assembly to a rotatable column, the mobile drive system further configured to move based on a degree of motion of the first movable component.

16. The mobile imaging system of claim 15, wherein the first movable component of the mobile drive system comprises the arm coupled to the rotatable column, the column coupled to and extending up from a frame of the mobile drive system.

17. The mobile imaging system of claim 16, wherein the arm is a telescoping arm configured to telescope toward the column in response to a push input on the hand-actuatable component of the second driving interface and to telescope away from the column in response to a pull input on the hand-actuatable component of the second driving interface, and the column is configured to rotate around a pivot point of the mobile drive system in response to rotational input on the hand-actuatable component of the second driving interface.

18. The mobile imaging system of claim 16, wherein the second driving interface comprises one or more sensors configured to detect the degree of motion of the arm, the one or more sensors including a first sensor positioned proximate the column and a second sensor positioned proximate the imaging assembly.

19. The mobile imaging system of claim 16, wherein the mobile drive system comprises a controller storing instructions in non-transitory memory executable by the controller to:
    determine the degree of motion of the arm based on output from the one or more sensors;
    responsive to the degree of relative motion reaching a first threshold value, drive one or more wheels of the mobile drive system to move the mobile drive system in a first direction; and
    responsive to the degree of motion reaching a second threshold value, different than the first threshold value, drive one or more wheels of the mobile drive system to move the mobile drive system in a second direction.

20. The mobile imaging system of claim 19, wherein the instructions are further executable to, responsive to the degree of motion being between the first threshold value and the second threshold value, not drive the one or more wheels of the mobile drive system.

* * * * *